US00PP28660P3

(12) United States Plant Patent
Valdez

(10) Patent No.: US PP28,660 P3
(45) Date of Patent: Nov. 21, 2017

(54) HYBRID TEA ROSE PLANT NAMED 'TEXMIRLAM'

(50) Latin Name: *Rosa hybrida*
Varietal Denomination: TEXmirlam

(71) Applicant: Texas Rose Ventures, LLC, Waddell, AZ (US)

(72) Inventor: Lawrence Valdez, Tyler, TX (US)

(73) Assignee: Texas Rose Ventures, LLC, Waddell, AZ (US)

( * ) Notice: Subject to any disclaimer, the term of this patent is extended or adjusted under 35 U.S.C. 154(b) by 0 days.

(21) Appl. No.: 14/757,220

(22) Filed: Dec. 7, 2015

(65) Prior Publication Data

US 2017/0231128 P1 Aug. 10, 2017

(51) Int. Cl.
*A01H 5/02* (2006.01)

(52) U.S. Cl.
USPC ..... Plt./138

(58) Field of Classification Search
USPC ..... Plt./101, 130, 137, 138
See application file for complete search history.

(56) References Cited

U.S. PATENT DOCUMENTS

PP23,476 P2 3/2013 Carruth

OTHER PUBLICATIONS

Certified Roses Inc. Invoice No. 0007394-IN, Order No. 0007829, Sold and Shipped to: Another Bloomin Nursery, 6 pages, order date Nov. 5, 2015.

*Primary Examiner* — Susan McCormick Ewoldt
(74) *Attorney, Agent, or Firm* — McKee, Voorhees & Sease, PLC

(57) ABSTRACT

A new variety of Hybrid Tea rose suitable for garden decoration, having intensely fragrant flowers of deep pink coloration.

1 Drawing Sheet

Classification: The present invention relates to a new *Rosa hybrida* plant.

Variety denomination: The new plant has the varietal denomination 'TEXmirlam'.

BACKGROUND OF THE INVENTION

This invention relates to a new and distinct variety of Hybrid Tea Rose. It has as its seed parent the variety an undisseminated seedling of unrecorded parentage and as its pollen parent a separate undisseminated seedling of unrecorded parentage.

SUMMARY OF THE INVENTION

Among the features which distinguish the new variety from other presently available and commercial rose cultivars known to the inventor are the following combinations of characteristics: 'TEXmirlam' has intense rose to fruit fragrance, its upright moderately tall growing habit with abundant, very full, high centered and elegant blooms on strong long stems.

The plant is an upright growing plant, suitable for outdoor garden decoration.

Asexual reproduction of the new variety by budding as performed in Maricopa County, Ariz., shows that the foregoing and other distinguishing characteristics come true to form and are established and transmitted through succeeding asexual propagations. 'TEXmirlam' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, an undisseminated seedling by the following combination of characteristics: whereas the seed parent bears mildly fragrant semi-double flowers (about 18 to 23 petals) of red coloration, 'TEXmirlam' bears intensely fragrant fully double flowers (about 38 to 43 petals) of deep pink coloration. The new variety has upright moderately tall growing habit (about 138 to 155 cm. in height) whereas the seed parent has a significantly taller, more upright habit (about 145 to 175 cm. in height.

The new variety may be distinguished from its pollen parent, an undisseminated seedling by the following combination of characteristics: whereas 'TEXmirlam' bears large flowers (about 10.5 to 12.0 cm. in diameter) of deep pink coloration. Whereas the pollen parent significantly smaller flowers (about 7.8 to 9.4 cm. in diameter) of lighter pastel pink coloration.

Whereas the pollen parent bears very glossy deep green foliage, the new seedling bears more matte, slightly lighter green foliage.

COMPARISON WITH THE CLOSEST COMMERCIALLY AVAILABLE CULTIVAR

The new variety may be distinguished from its closest commercially available cultivar, 'WEKmerewby' (U.S. Plant Pat. No. 23,476) by the following combination of characteristics:

Whereas 'TEXmirlam' bears fully double flowers (about 38 to 49 petals) of deep pink coloration, 'WEKmerewby' bears double flowers of significantly lighter pink coloration. The new variety has intense rose to fruit fragrance whereas the closest commercially available cultivar has a very strong damask to somewhat fruity fragrance.

The new variety has very strong long stems whereas the closest commercially available cultivar has weaker necks sometimes leading to nodding blooms.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 to 3 year-old rose plants of the new variety grown outdoors in Tyler, Tex. in the month of October. Phenotypic expression may vary with environmental, cultural and climatic conditions, as well as differences in conditions of light and soil.

FLOWER

The new variety usually bears its flowers singly. Flowers are borne on strong long stems (about 38 to about 67 cm.). Outdoors, the plant blooms abundantly and nearly continuously during the growing season. The flowers have an intense rose to fruit fragrance.

BUD

The peduncle is about 5.5 to about 8.0 cm. in length, of average (about 0.3 to about 0.4 cm. in diameter), and usually erect, but sometimes slightly bending. It is almost entirely smooth, with some stipitate glands and some hairs. Peduncle color is near 144A.

Before the calyx breaks, the bud is about 1.9 to about 2.4 cm. in diameter at the widest point, about 1.4 to about 1.9 cm. in length, and ovoid in shape with a conspicuous neck. The surface of the bud bears between 4 to 6 foliaceous appendages, usually with slender foliaceous parts extending beyond the tip of the bud about ¼ or more of its length. Bud color is between 144B and 144C.

The sepals are about 2.3 to about 2.7 cm. in length and about 0.8 to about 1.0 cm. in width at the widest point. The outer surface color of the sepal is near between 144B and 144C. The outer surface of the sepal is moderately smooth. The inner surface color of the sepal is near 147C. The inner surface of the sepal is covered with fine wooly tomentum; sepal margins are lined with many stipitate glands.

The receptacle of the flower is of medium length (about 0.4 to about 0.6 cm.) and average in caliper (about 0.9 to about 1.1 cm. in diameter). The receptacle is urn-shaped in form. Its surface is very smooth with thick dry fleshy walls. The receptacle color is near between 144B and 144C.

As the petals open (after the calyx breaks), the bud is about 2.0 to about 2.6 cm. in diameter at the widest point, about 1.5 to about 2.0 cm. in length, and moderately ovoid in form. The color of the under and upper surfaces of the newly opened petals is near between 58A and 64B. At the point where the petal attaches, there is a moderately small zone of between 11D and 155C. The color of the upper surfaces of the newly opened petals is near between 61B and 63B. At the point where the petal attaches, there is a very small large zone of near between 12B and 155B.

BLOOM

When fully open, the bloom ranges from about 10.5 to about 12.0 cm. in diameter. Petalage is very full with about 38 to 49 petals and about 3 to 4 petaloids irregularly arranged. When partially open, the bloom form is very high centered, and the petals are somewhat tightly spiraled with petal edges somewhat reflexed outward. When fully open, the bloom form is very full, and the petals are moderately loosely cupped with petal edges somewhat reflexed outward.

PETALS

The substance of the petals is somewhat heavy and of medium thickness, with upper surfaces slightly somewhat velvety and under surfaces somewhat satiny. The petals are about 4.2 to about 5.7 cm. in length and about 3.2 to about 6.1 cm. in width at the widest point. Petal margins are somewhat entire.

The outer petals are nearly round to ovate in shape with moderately rounded apices that sometimes exhibit one to two notches.

The inner petals are somewhat more narrowly obovate in shape with apices somewhat rounded to flat and sometimes exhibit one to two notches.

Petaloids are about 1.9 to about 2.5 cm. in length and about 1.7 to about 2.1 cm. in width at the widest point. Petaloids are shaped somewhat irregular to obovate.

NEWLY OPENED FLOWER

The under surface color of the outer petals is near between 58A and 64B. At the point where the petal attaches, there is a very small large zone of near between 12B and 155B. The upper surface color of the outer petals is near between 74B and 66B. At the point where the petal attaches, there is a very small zone of between 12B and 155B.

The under surface color of the intermediate petals is near between 58A and 64C. The upper surface color of the intermediate petals is near between 63A and 68A.

The under and upper surface color of the inner petals is near between 66A and 67A.

The under and upper surface colors of the petaloids are similar in coloration to the upper and under surfaces of the intermediate and inner petals.

The general tonality of the newly opened flower is near between 66A and 67A.

THREE-DAY-OLD FLOWER

The under surface color of the outer, intermediate and inner petals is near between 66B and 67B. At the point where the petal attaches, there is a very small zone of near between 12B and 155B.

The upper surface color of the outer, intermediate and inner petals is between 66A and 67A.

The under and upper surface colors of the petaloids are similar in coloration to the upper and under surfaces of the intermediate and inner petals.

The general tonality of the three-day-old flower is near between 66A and 67A.

On the spent bloom, the petals usually drop off cleanly, and are not particularly affected by cold, hot, wet, or dry weather.

In September in Tyler, Tex., blooms on the bush growing outdoors generally last about five to seven days. Cut roses from plants grown outdoors and kept at normal indoor living temperatures generally last about five to seven days.

MALE REPRODUCTIVE ORGANS

Stamens are average to many in number (average about 110) and are arranged regularly about the pistils. The filaments are of somewhat irregular length (about 0.9 to about 1.3 cm.) many without anthers. Filaments are near between 11B and 11C in color. The anthers are somewhat medium size for the class and all open approximately at the same time. Anther color when immature is near 12B on the external part and near 11B on the internal part. Anther color at maturity is near 12D on the external part and near 166B on the internal part. Pollen is somewhat moderate to abundant and near 11C in color.

FEMALE REPRODUCTIVE ORGANS

Pistils vary in number (average about 75). The styles are moderately uneven, somewhat short to average in length (about 0.4 to about 0.6 cm.), somewhat thin to average in caliper, and loosely separated to. Stigma color is near between 4C. Style color is near 4D. Ovaries are usually all enclosed in the calyx.

Hips have not been observed on this variety when grown in Tyler, Tex.

The seeds are irregularly rounded, smooth in texture, approximately 10 to about 16 per hip, about 0.4 to about 0.6 cm. in diameter at the widest point and near 165D in color.

FOLIAGE

The compound leaves are usually comprised of three to five leaflets and are borne very abundantly. The five-leaflet leaves are about 8.9 to about 13.6 cm. in length and about 8.4 to about 12.1 cm. in width at the widest point, somewhat heavy to leathery in texture, and somewhat semi-glossy to matte in finish on the upper side and somewhat matte in finish on the underside. The terminal leaflets are about 4.5 to about 7.2 cm. in length and about 3.8 to about 4.8 cm. in width at the widest point, shaped somewhat oval with somewhat round to slightly acute bases. Their margins are very usually simply serrate.

The upper surface color of the mature leaf is near between NN137B and 147A. The under surface color of the mature leaf is near between 146B and 148A. The upper surface color of the young leaf is between 137A and 147B, often lightly suffused with near 184B. The under surface color of the young leaf is near 144B, usually lightly suffused with near 181B.

The rachis is average to heavy in caliper and moderately smooth. The upper side somewhat shallowly grooved with few stipitate glands on the edges of the grooves. The under side of the rachis is moderately smooth with few stipitate glands and very sometimes two or three moderately small prickles. The rachis color is near 144C on the under and upper side.

The stipules are about 1.4 to about 1.6 cm. in length and somewhat narrow in width (about 0.7 to about 0.8 cm.) with moderately short to medium length straight points that usually sometime turn out at an angle of more than 45 degrees. The under and upper surface color of the stipule is near 144A.

The petiole is average caliper and very smooth rough. The upper side is moderately shallowly grooved with few stipitate glands on the edges of the grooves. The under side of the petiole is very smooth with few stipitate glands. The petiole is about 0.2 to about 0.3 cm. in length and about 0.15 to about 0.20 cm in width at the widest point. The petiole color is near 144A on the under and upper sides.

The plant displays an above average degree of resistance to powdery mildew, black spot and rust as compared to other commercial varieties grown under comparable conditions in Tyler, Tex. The plant's winter hardiness and drought/heat tolerance are yet to be determined.

GROWTH

The plant has a moderately tall upright growth habit (about 138 to about 155 cm. in height and about 85 to about 110 cm. spread at the widest point), with very full branching. It displays very vigorous growth and the canes are of medium to heavy caliper for the class (about 1.1 to about 1.4 cm. in diameter at the widest point).

The color of the major stems is near 146D. They bear many large prickles that are about 0.7 to about 0.9 cm. in length. The large prickles are almost straight to angled slightly downward with a medium length and somewhat broad; prickle color is near between 164B and 165C. The major stem bears few small prickles of similar shape and coloration.

The color of the branches is near between 147C and 146D. They bear some large prickles which are of similar size and shape to the large prickles on the major stems; prickle color is near between 164BC and 165C. The branches bear few small prickles of similar shape and coloration.

The color of the new shoots is near 144B often lightly suffused with between 183A and 185A. They bear some many large prickles which are of similar size and shape to the large prickles on the major stems; prickle color is near 153B often lightly suffused between 185C and 183C. The shoots bear some small prickles of similar shape and coloration.

I claim:

1. A new and distinct Hybrid Tea rose plant of the variety substantially as described and illustrated herein.

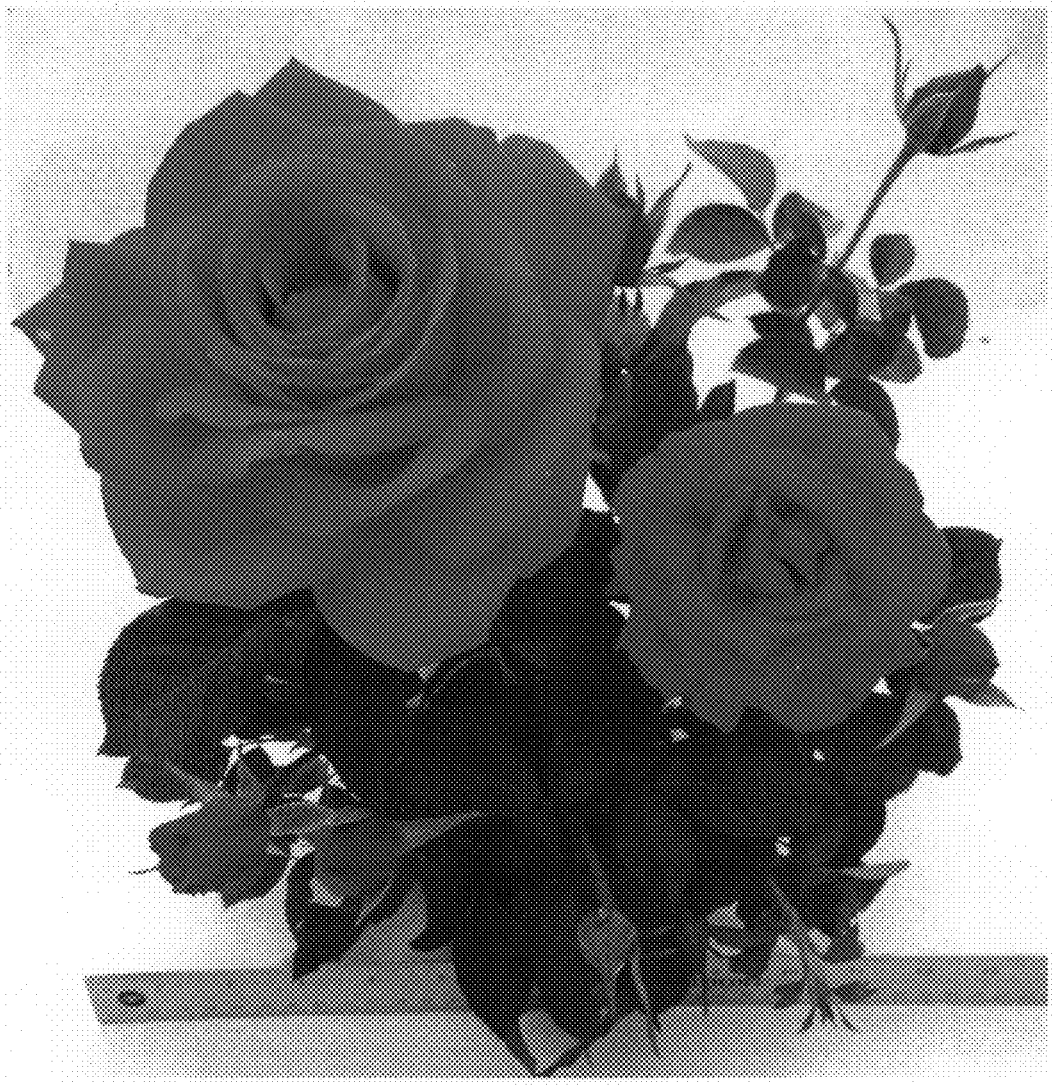

* * * * *